United States Patent [19]

Vogel et al.

[11] 4,168,965
[45] Sep. 25, 1979

[54] 2,6-DIETHYL-N-(2'-N-PROPOXYETHYL)-CHLOROACETANILIDE FOR SELECTIVELY COMBATING WEEDS

[75] Inventors: Christian Vogel, Binningen; Rudolf Aebi, Basel, both of Switzerland

[73] Assignee: Ciba-Geigy Corporation, Ardsley, N.Y.

[21] Appl. No.: 893,541

[22] Filed: Apr. 5, 1978

Related U.S. Application Data

[63] Continuation-in-part of Ser. No. 678,775, Apr. 20, 1976, abandoned, which is a continuation-in-part of Ser. No. 512,285, Oct. 4, 1974, abandoned, which is a continuation-in-part of Ser. No. 366,955, Jun. 3, 1973, abandoned.

[30] Foreign Application Priority Data

Jun. 6, 1972 [CH]  Switzerland ........................ 8345/72
Mar. 30, 1973 [CH]  Switzerland ........................ 4607/73

[51] Int. Cl.² ..................... A01N 9/20; C07C 103/375
[52] U.S. Cl. .................................. 71/118; 260/562 B
[58] Field of Search ....................... 71/118; 260/562 B

[56] References Cited

U.S. PATENT DOCUMENTS

| 3,442,945 | 5/1969 | Olin | 71/118 X |
| 3,547,620 | 12/1970 | Olin | 71/118 |
| 3,663,200 | 5/1972 | Olin | 71/118 |
| 3,739,024 | 6/1973 | Chupp | 260/551 S |

FOREIGN PATENT DOCUMENTS

1903198  8/1970  Fed. Rep. of Germany .
1283163  6/1972  United Kingdom .

*Primary Examiner*—Catherine L. Mills
*Attorney, Agent, or Firm*—Harry Falber

[57] ABSTRACT

2,6-diethyl-N-(2'-propoxyethyl)-chloroacetanilide is an outstanding selective herbicide for combating weeds in rice cultures.

3 Claims, No Drawings

2,6-DIETHYL-N-(2'-N-PROPOXYETHYL)-CHLOROACETANILIDE FOR SELECTIVELY COMBATING WEEDS

CROSS-REFERENCE

This application is a continuation-in-part of our application Ser. No. 678,775, filed Apr. 20, 1976, now abandoned, which in turn is a continuation-in-part of abandoned application Ser. No. 512,285, filed Oct. 4, 1974, which in turn is a continuation-in-part of abandoned application Ser. No. 366,955, filed June 3, 1973.

The invention is directed to 2,6-diethyl-N-(2'-n-propoxyethyl)-chloroacetanilide of the formula I

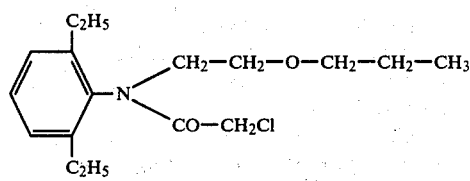

to herbicidal compositions which contain this product as active ingredient and to a method of selectively combating undesirable plant growth in rice crops which comprises applying compound I to the rice growing area.

The active substance I according to the invention is a stable compound with prolonged activity in the soil and possesses very good herbicidal properties against a broad spectrum of weeds contaminating rice crops. At the same time this compound is excellently tolerated by rice plants. Among the weeds susceptible to compound I the following should be mentioned. Echinochloa sp., Cyperus sp., Scirpus sp., *Dinebra retroflexa, Eleusine indica, Monochoria vaginalis, Fimbristylis miliacea, Eleocharis acicularis, Ammannia senegalensis, Eclipta alba, Rotala indica, Lindernia pyxidaria,* Ludwigia sp., *Dopatrium junceum, Galinsoga parviflora, Alisma canaliculatum, Elatine triandra,* Digitaria sp., *Scirpus hotarui,* Borreria sp., *Cyperus serotinus, Bidens pilosa* etc.

Monochoria and Scirpus sp. belong to the group of weeds which cause severe problems of contamination of rice fields because of their resistency to most of the market herbicides. It should, be emphasized, therefore, that compound I displays a far better activity against these and the other above mentioned weeds at significantly lower rates of application than the standard products.

In U.S. Pat. No. 3,547,620 haloacetanilides are disclosed as selective herbicides. In col. 14, lines 5 to 9, however, the following statement is made relating to the type of structure which is responsible for the practical utility of this class of compounds:

"The difference in herbicidal effectiveness is directly related to the presence of an alkoxymethyl, instead of an alkoxyethyl or alkoxypropyl group, on the nitrogen atom of the acetanilide."

The closest homologs to compound I of this invention disclosed in U.S. Pat. No. 3,547,620 are compounds Nos. 59 and 66 which are referred to herein as Nos. C and B respectively having the formulae

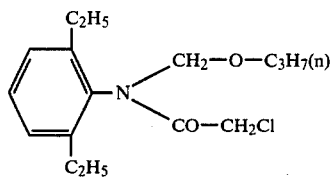

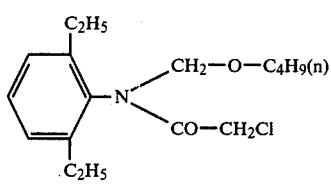

In U.K. Pat. No. 1,283,163 it is taught to use certain chloroacetanilides for purposes of controlling weeds mainly in rice crops in admixture with the herbicide 3',4'-dichloropropionanilide in order to broaden the limited spectrum of activity. One example of a chloroacetanilide disclosed in this Patent is compound B, another is 2',6'-diethyl-N-(2-n-butoxyethyl)-2-chloroacetanilide of the formula

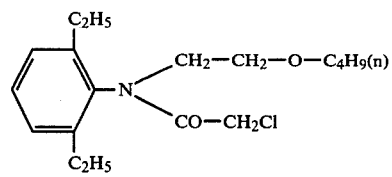

which is referred to herein as compound A. In view of the teaching of the U.S. Pat. No. 3,547,620 compound A belongs to the group which would be expected to have inferior herbicidal properties. In U.K. Pat. No. 1,283,163 this expectation is confirmed by the necessity of using another herbicide in addition, possibly to achieve practical utility.

Contrary to what would be expected from the structural homologous pattern of compounds A, B and C and from the teaching of the U.S.-reference in combination with the U.K.-reference, compound I has surprisingly been found to exhibit a completely distinctive pattern of behaviour, which renders it vastly more suitable for practical utility.

The active substance I is applied either before or at the germination of the rice plants and of the weeds; preemergence application is preferred. Postemergence application is recommendable only in cases of paddy rice where emerged weeds are still under the water. The rates of application in upland rice and paddy rice are between 0.1 and 1.25 kg of active substance per hectare, preferably as low as 0.25 to 0.9 kg of active substance per hectare. As a rule, the sufficiently acting prelat-emergent herbicide compound I avoids the necessity of further herbicides post-emergent application.

Furthermore, compound I possesses a favorably low fish toxicity, thus being very suitable for paddy rice cultures in Asia which are very often the habitat of fish.

The new chloroacetanilide of the formula I is manufactured by known methods, e.g. by reacting N-(2'-n-propoxyethyl)-2,6-diethylaniline of the formula II

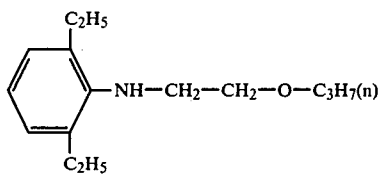

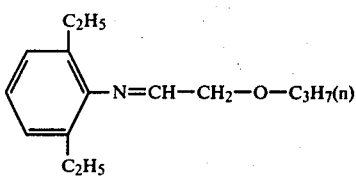

with a chloroacetylating agent, preferably an anhydride or halide of chloroacetic acid.

It is also possible to manufacture the compound of the formula I in such a way that 2,6-diethyl-aniline is reacted with 2-haloethanol or ethylene oxide to introduce the hydroxyalkyl chain —CH$_2$—CH$_2$—OH, then the resulting compound of the formula IIa

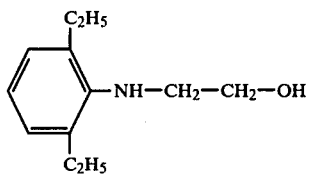

is chloroacetylated, preferably with an anhydride or halide of chloroacetic acid, and finally the still free OH group is etherified in acid medium (e.g. HCl, H$_2$SO$_4$) under mild conditions and in conventional manner with n-propanol.

The reactions can be carried out in the presence or absence of solvents or diluents which are inert towards the reactants. Examples of suitable solvents or diluents are: aliphatic, aromatic or halogenated hydrocarbons, such as benzene, toluene, xylene, petroleum ether, chlorobenzene, methylene chloride, ethylene chloride, chloroform; ethers and ethereal compounds, such as dialkyl ethers, dioxan, tetrahydrofuran, nitriles, such as acetonitrile; N,N-dialkylated amides, such as dimethyl formamide; also dimethyl sulphoxide, and also mixtures of these solvents.

As suitable chloroacetylating agents there are preferably used chloroacetic anhydride, and chloroacetic halides, such as chloroacetyl chloride. However, it is also possible to carry out the reaction with chloroacetic acid or its esters. The reaction temperatures are between 0° and 200° C., preferably between 20° and 100° C. Often, especially if chloroacetyl halides are used, the chloroacetylation is carried out in the presence of an acid binding agent. Suitable acid binding agents are: tertiary amines, such as trialkylamines, e.g. triethylamine, pyridine and pyridine bases, or inorganic bases, such as the oxides and hydroxides, hydrogen carbonates and carbonates of alkali and alkaline earth metals. Furthermore, it is also possible to use 2,6-diethylaniline as acid binding agent, in which case it must be used in excess.

Compounds homologous to formula II and hydroxyalkyl derivatives homologous to formula IIa are known, e.g. from U.S. Pat. No. 2,381,071, 2,759,943 as well as from Am. Soc. 84,743 and Bull. Soc. Chim. France 1962, 303 and 1965, 2037. These starting materials can be manufactured easily by one of the following known methods, for example:

(a) by condensation of 2,6-diethylaniline with n-propoxyacetaldehyde and simultaneous or subsequent catalytic hydrogenation of the resulting azomethine of the formula III or (b) by reaction of 2,6-diethylaniline with a compound of the formula IV $$Y-CH_2-CH_2-O-CH_2-CH_2-CH_3 \qquad (IV)$$

Y represents a halogen atom or another acid radical, in particular an arylsulphonic acid radical. Homologs corresponding to formula IV with benzenesulphonic acid radicals Y are described e.g. in Can. J. Chem. 33, 1207, and those with tosyloxy radicals (CH$_3$—C$_6$H$_4$—SO$_3$—) in British Pat. No. 869,083.

The following Example 1 illustrates the invention, including the manufacture of the starting material. The temperatures are given in centigrades.

EXAMPLE 1

(a) Manufacture of the intermediate product 20 kg of toluene and 10.5 kg of diethylaniline are placed in a 100 liter enamel vessel the atmosphere of which has been freed from oxygen by the passage of nitrogen. After heating the mixture up to 95°–100° C. 20 kg of p-toluenesulfonic-acid-2-propylethylester are added while stirring over a period of 90 minutes the temperature being kept at the starting level. The mixture is stirred for a further 48 hours at 105° C. and then cooled.

The reaction mixture is transferred into a solution containing 12.3 kg of sodium hydroxide (30%) and 20 kg of water in a second 100 liter enamel vessel, whereby the temperature is held below 60° C. After stirring for one hour at 40° C. the content of the vessel is separated into its organic and the aqueous layers. The organic layer is again washed with 10 kg of water for 15 minutes and subsequently evaporated at 60°–65° C./20 Torr. 15 kg crude N-(2-propoxyethyl)-2',6'-diethylaniline are obtained and purified by rectification.

(b) Manufacture of 2,6-diethyl-N-(2'-propoxyethyl)-N-chloroacetanilide 5.18 kg of N-(2-propoxyethyl)-2',6'-diethylaniline, 2.57 kg of sodium carbonate and 14 kg toluene are placed in a 50 liter dry enamel vessel (with refluxing device, ice/salt cooler and acid absorber) the atmosphere of which has been freed from oxygen by the passage of nitrogen.

The mixture is cooled down to 0° C. and a solution consisting of 4 kg toluene and 2.74 kg of chloroacetyl chloride is added dropwise thereto over a period of 2 hours. The internal temperature of this chloroacetylation step is kept below 5° C. by means of an ice/salt cooler. After the addition of chloroacetyl chloride the chloroacetylation is completed by further stirring over a period of 3 hours at steady temperature. The mixture is subsequently emulsified at room temperature with 20 kg of water. The salts obtained (NaHCO$_3$ and NaCl) are dissolved. The content of the vessel is forced into a 100 liter glass separator by means of a nitrogen current and the two phases allowed to separate (pH 8-9).

The toluene layer is washed twice with 4 kg of water until neutral and evaporated. The residue yields 6.85 kg (=95% of theoretical amount) of 2,6-diethyl-N-(2'-propoxy-ethyl)-N-chloroacetanilide, $n_D^{20}$ 1.5204.

EXAMPLE 2

Herbicidal activity

In Balong Gandu, Indonesia, the following comparative test was carried out under natural conditions at about 30° C. during July to September. Rice was seeded into a wet nursery and after emergence the seedlings in the 3- to 4-leaf stage were transplanted by hand into 4 square meter plots and flooded. 4 days after transplanting each plot was treated with granules of the test substance. The rates corresponded to 0.125, 0.25, 0.5, 1.0 and 2.0 kg active ingredient per hectare. Untreated plots served as control. The 2kg rate exemplified an overdosis. During July and August the following natural occuring weeds emerged:

*Echinochloa crus-galli* = barnyard grass
*Monochoria vaginalis* = Monochoria
*Cyperus difformis* = umbrella sedge
*Fimbristylis miliacea* = Fimbristylis
*Scirpus lateriflorus* = bulrush The evaluation took place 62 days after treatment. The results are given in percent of plant damage in the following table.

Table

| Rate [kg a.i. per hectare] | Compound | Rice | Echino-chloa | Mono-choria | Cyperus | Fimbri-stylis | Scir-pus |
|---|---|---|---|---|---|---|---|
| 0.125 | I | 0 | 80 | 35 | 75 | 90 | 40 |
| | A | 0 | 25 | 0 | 80 | 65 | 0 |
| | B | 0 | 30 | 0 | 80 | 40 | 0 |
| | C | 5 | 50 | 60 | 80 | 70 | 45 |
| 0.25 | I | 0 | 90 | 75 | 100 | 100 | 50 |
| | A | 0 | 45 | 15 | 90 | 90 | 0 |
| | B | 0 | 70 | 0 | 85 | 40 | 0 |
| | C | 20 | 95 | 80 | 90 | 95 | 80 |
| 0.5 | I | 0 | 95 | 75 | 100 | 100 | 65 |
| | A | 0 | 70 | 30 | 95 | 100 | 0 |
| | B | 0 | 70 | 0 | 80 | 70 | 0 |
| | C | 35 | 95 | 85 | 100 | 95 | 70 |
| 1.0 | I | 0 | 100 | 95 | 100 | 100 | 100 |
| | A | 0 | 90 | 50 | 100 | 95 | 50 |
| | B | 10 | 70 | 50 | 90 | 65 | 20 |
| | C | 50 | 100 | 90 | 100 | 100 | 100 |
| 2.0 | I | 15 | 100 | 95 | 100 | 100 | 100 |
| | A | 25 | 95 | 90 | 100 | 100 | 90 |
| | B | 40 | 100 | 95 | 95 | 100 | 100 |
| | C | 65 | 100 | 90 | 100 | 100 | 100 |

Comments

We see clearly that at 0.25 kg a.i./ha compound I gave good to excellent control of Echinochloa, Cyperus and Fimbristylis, while compound B did not attain this level of effect even with 1 kg a.i./ha. Compound A resembles product B closely in the weed species it can control and in its percentage control figures at each of the rates tested.

A part from the remarkable rice tolerance compound I is thus stronger than compounds A and B by a factor of at least 4, and probably 5 or 6.

Compound C is useless for rice protection because of its unselective phytotoxicity.

EXAMPLE 3

Fish toxicity

The compound of the invention and the comparative compounds A and B were tested in accordance with a method which is a modification of the procedure proposed by the United States Department of the Interior Fish and Wildlife Service, [reported in "Procedure for Evaluation of Acute Toxicity of Pesticides to Fish and Wildlife" of December 14, 1964.]

(a) Fish toxicity was tested in three species:
1. Rainbow trout
   Average Weight: 8 g
   Average Length: 89 mm
2. Crucian carp
   Average Weight: 3,5 g
   Average Length: 59 mm
3. Catfish
   Average Weight: 1.3 g
   Average Length: 50 mm Prior to testing, the fish were adapted to laboratory conditions for a minimum of 10 days. They were kept in 250 lit. glass tanks containing normal drinking water which was aerated and filtered continuously through a filter bed of activated charcoal. The fish were fed daily. Prior to testing the food was withdrawn for 3 days.

Overall mortalities in stocks were well below 10% and no deaths occurred during the 10 days prior to testing. All fish were in good condition and free from disease.

(b) Testing Procedures:

The fish were placed in glass tanks, of 12 liter capacity. Testing was performed in reconstituted water prepared from deionised water to which salts were added in the following amount per liter:
30 mg calcium sulphate
30 mg magnesium sulphate
48 mg sodium carbonate
3 mg potassium chloride The fish were tested at about 15° C. (trout, carp) and at about 22° C. (catfish). With exception of experiments on trout the water was not aerated during testing. Four fish were placed in each tank resulting in the following weights of fish per volume of water:

Rainbow trout - 2.5 g/liter
Crucian carp - 1.2 g/liter
Catfish - 0.4 g/liter

Various concentrations of the active substances were prepared by adding the substance dissolved in acetone at the appropriate amount ensuring that the total volume in each vessel remained the same. The corresponding volume of acetone was added to the vessels containing the control group.

Oxygen dissolved in the water and pH were monitored at 24 hour intervals throughout the 96 hour testing period. 12 fish were used per active substance and per concentration.

The test resulted in the following $LC_{50}$ data for each of the active substances (measured in ppm):

|         | Compound I | Compound A | Compound B |
|---------|------------|------------|------------|
| Trout   | 3.0        | 1.8        | 0.7        |
| Carp    | 3.0        | 2.0        | 0.7        |
| Catfish | 2.6        | 1.3        | 0.3        |

Among the homologs, compound I clearly exhibited the best fish toxicity. Measured against the trade product compound B (Butachlor) compound I was less fish-toxic by at least a factor of 4. Not only is the fish toxicity of compound I at least 4 times less than that of compound B, but also, as is demonstrated in Example 2, its use rates in practice are considerably lower. The risk to aquatic animals is thus even further reduced. In South-East Asia, it is common to find fresh water fish being bred and encouraged to develop in paddy fields, in the canals which drain excess water from long lines of fields at the same level, and in reservoirs and ponds both above and below the contoured rice fields.

The agents according to the invention are manufactured in known manner by intimately mixing and/or grinding the active substance of the formula I with the suitable carriers, optionally with the addition of dispersants or solvents which are inert towards the active substance. The active substance may take and be used in the following forms:
Solid forms:
  dusts, tracking agents, granules, coated granules, impregnated granules and homogeneous granules.
Liquid forms:
  (a) active substances which are dispersible in water: wettable powders, pastes, emulsions;
  (b) solutions.

To manufacture solid forms (dusts, tracking agents), the active substance is mixed with solid carriers. Suitable carriers are, for example: kaolin, talcum, bolus, loess, chalk, limestone, ground limestone, attaclay, dolomite, diatomacous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.1% to 80%.

To these mixtures can also be added additives which stabilize the active substance and/or non-ionic, anionic and cationic surface active substances, which for example improve the adhesion of the active ingredients on plants or parts of plants (adhesive and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ether having 5 to 20 ethylene oxide radicals per molecule and 8 to 18 carbon atoms in the fatty alcohol moiety, condensation product of urea and formaldehyde, and also latex products. Preferred dispersions (suspensions and emulsions) are manufactured by mixing or grinding the active substance with carriers accompanied by the addition of dispersing agents and solvents, in the process of which there result firstly dispersible active substance concentrations, such as wettable powders and emulsifiable concentrates.

The water-dispersible concentrates of the active substance i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents. The active substance concentrations in these agents are from 5–80%.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salt of oleoyl methyl tauride, ditertiary acetalene glycols, dialkyl dilauryl ammonium chloride and fatty acid alkali and alkaline earth metal salts.

Suitable anti-foam agents are silicones. The active substance is so mixed, ground, sieved and strained with the additives mentioned above that, in wettable powders, the solid particle size of from 0.02 to 0.04 and in pastes, of 0.03 is not exceeded. To produce emulsifiable concentrates and pastes, dispersing agents such as those given in the previous paragraphs, organic solvents and water are used. Examples of suitable solvents are the following: alcohols, benzene, xylenes, toluene, dimethyl sulphoxide, N,N-dialkylated amides, N-oxides of amines (whereas N-oxides of trialkylamines are preferred), and mineral oil fractions boiling between 120° and 350° C. The solvents must be practically odorless, not phytotoxic, inert to the active substance and not readily inflammable.

Furthermore, the agents according to the invention can be applied in the form of solutions. For this purpose the active substance of formula I is dissolved in suitable organic solvents, mixtures of solvents or in water. Aliphatic and aromatic hydrocarbons, chlorinated derivatives thereof, alkyl naphthalenes and mineral oils singly or in admixture, can be used as organic solvents. The solutions contain the active substance in a concentration range from 1% to 20%.

The agents described according to the invention can be mixed with other biocidally active substances or agents. Thus in order to broaden the activity spectrum the new agents may contain, for example, insecticides, fungicides, bactericides, fungistatics, bacteriostatics, nematocides or further herbicides, in addition to the cited active substance of the formula I. The agents according to the invention may also contain plant fertilisers, trace elements etc.

The active substance of the formula I can, for example, be formulated as follows. The parts denote parts by weight.

Granules

The following substances are used to manufacture 5% granules:
5 parts of compound I
0.25 parts of epichlorohydrin,
0.25 parts of cetyl polyglycol ether,
3.50 parts of polyethylene glycol ether,
91 parts of kaolin (particle size: 0.3–0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable powder

The following constituents are used to manufacture (a) a 50%, (b) a 25% and (c) a 10% wettable powder:
(a)
  50 parts of compound I
  5 parts of sodium dibutylnaphthalene sulphonate,
  3 parts of naphthalenesulphonic acid/phenolsulphonic acid/formaldehyde condensate (3:2:1),
  20 parts of kaolin,
  22 parts of Champagne chalk;
(b)
  25 parts of compound I
  5 parts of oleylmethyltaurid-sodium-salt,
  2.5 parts of naphthalenesulphonic acid/formaldehyde condensate,
  0.5 part of carboxymethyl cellulose,
  5 parts of neutral potassium-aluminium-silicate,
  62 parts of kaolin;
(c)
  10 parts of compound I
  3 parts of a mixture of the sodium salts of saturated fatty alcohol sulphates,
  5 parts of naphthalenesulphonic acid/formaldehyde condensate,
  82 parts of kaolin.

The indicated active substance is applied to the corresponding carriers (kaolin and chalk) and then these are mixed and ground, to yield wettable powders of excellent wettability and having an excellent capacity for forming suspensions. By diluting these wettable powders with the 10-fold amount of water it is possible to obtain suspensions of any desired concentration.

Paste

The following substances are used to manufacture a 45% paste:
45 parts of compound I
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of polyethylene glycol,
23 parts of water.

The active substance is intimately mixed with the addition in appropriate devices and ground. A paste is obtained from which, by diluting it with water, is possible to manufacture suspensions of every desired concentration of active substance.

Emulsion Concentrate

To manufacture a 25% emulsion concentrate
25 parts of compound I
5 parts of mixture of nonylphenolpolyoxy-ethoxyethylene and calcium dodecylenesulphonate,
35 parts of 3,5,5-trimethyl-2-cyclohexan-1-one,
35 parts of dimethyl formamide,
are mixed together. This concentrate can be diluted with water to give emulsions in desired concentrations.

What we claim is:

1. The compound 2,6-diethyl-N-(2'-n-propoxyethyl)-chloroacetanilide of the formula

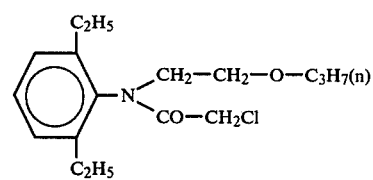

2. A herbicidal composition containing as active substance a herbicidally effective amount of the compound 2,6-diethyl-N-(2'-n-propoxyethyl)-chloroacetanilide, together with a suitable carrier therefor.

3. A method of selectively combating undesirable plant growth in rice crops, which comprises applying to the area to be treated an effective amount of 2,6-diethyl-N-(2'-n-propoxyethyl)-chloroacetanilide.

* * * * *